(12) United States Patent
Mansfield et al.

(10) Patent No.: US 7,960,391 B2
(45) Date of Patent: Jun. 14, 2011

(54) HETEROCYCLYLETHYLBENZAMIDE DERIVATIVES

(75) Inventors: Darren Mansfield, Bergisch Gladbach (DE); Pierre-Yves Coqueron, Lyons (FR); Heiko Rieck, Burscheid (DE); Philippes Desbordes, Lyons (FR); Alain Villier, Collonges au Mont d'Or (FR); Marie-Claire Grosjean-Cournoyer, Curis au Mont d'Or (FR); Pierre Genix, Lyons (FR)

(73) Assignee: Bayer Cropscience AG (DE)

( * ) Notice: Subject to any disclaimer, the term of this patent is extended or adjusted under 35 U.S.C. 154(b) by 654 days.

(21) Appl. No.: 11/919,598

(22) PCT Filed: May 2, 2006

(86) PCT No.: PCT/EP2006/061952
§ 371 (c)(1),
(2), (4) Date: Feb. 15, 2008

(87) PCT Pub. No.: WO2006/117356
PCT Pub. Date: Nov. 9, 2006

(65) Prior Publication Data
US 2009/0093490 A1     Apr. 9, 2009

(30) Foreign Application Priority Data

May 3, 2005   (EP) ..................... 05356075

(51) Int. Cl.
*A01N 43/54*     (2006.01)
*C07D 239/24*    (2006.01)
*C07D 237/06*    (2006.01)
*C07D 241/10*    (2006.01)

(52) U.S. Cl. ........ 514/256; 514/247; 544/334; 544/224; 544/409

(58) Field of Classification Search ............... 514/252.1, 514/247, 256, 252.01; 544/334, 224, 409
See application file for complete search history.

(56) References Cited

U.S. PATENT DOCUMENTS
7,723,364 B2 * 5/2010 Mansfield et al. ............ 514/357

FOREIGN PATENT DOCUMENTS

| | | |
|---|---|---|
| DE | 2706179 A1 | 8/1977 |
| EP | 1074546 | 2/2001 |
| FR | 1476925 | 4/1967 |
| JP | 2003128639 A | 5/2003 |
| WO | WO 99/42447 | 8/1999 |
| WO | WO 01/11965 | 2/2001 |

OTHER PUBLICATIONS

Patent Abstracts of Japan, vol. 2003, No. 09, Sep. 3, 2003 & JP 2003 128639 A (Sankyo Co. Ltd.) May 8, 2003, abstract.
Database CA [Online] Chemical Abstracts Service, Columbus, OH; 1959 Hadacek, J. et al: "Synthesis of 3-mercapto-5-hydroxy-6-(.beta.-aminoethyl)-1,2,-4-triazine", XP2379351, Database Accession No. 1959:89464, abstract, & Pharmazie, 14 19-21 CODEN: PHARAT; ISSN: 0031-7144, 1959.
Nils Lofgren & Hans Wahlstam: "Syntheses of N-[(4-morpholinyl)alkyl]benzamides", Acta Chem. Scand., vol. 15, 1961, pp. 1467-1476, XP009066039.
Database CA [Online] Chemical Abstracts Service, Columbus, OH; 1960 Hadacek, J. et al.: "The applicability of the Wolff-Liridehayn method in the chemistry of asymmetric triazines" XP002379350, Database Accession No. 1960:118361, abstract & Spisy Prirodovedecke Fak. Univ. BRNE 15-22; 1959.

* cited by examiner

*Primary Examiner* — Sreeni Padmanabhan
*Assistant Examiner* — Sahar Javanmard
(74) *Attorney, Agent, or Firm* — Ostrolenk Faber LLP

(57) ABSTRACT

A compound of general formula (I):

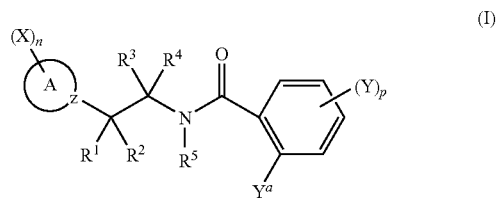

A process for preparing this compound.
A fungicide composition comprising a compound of general formula (I).
A method for treating plants by applying a compound of general formula (I) or a composition comprising it.

13 Claims, No Drawings

HETEROCYCLYLETHYLBENZAMIDE DERIVATIVES

CROSS-REFERENCE TO RELATED APPLICATIONS

The present application is a 35 U.S.C. §371 national phase conversion of PCT/EP2006/061952 filed 2 May 2006, which claims priority of European Application No. 05356075.1 filed 3 May 2005.

The present invention relates to novel heterocyclylethylbenzamide derivatives, their process of preparation, their use as fungicides, particularly in the form of fungicidal compositions, and methods for the control of phytopathogenic fungi of plants using these compounds or their compositions.

International patent application WO 01/11965 discloses a broad family of fungicidal compounds in which the 2-pyridyl group is substituted by at least one halogenoalkyl group. This document does not disclose neither it covers heterocyclylethylbenzamide derivatives according to the present invention.

It is always of high-interest in the field of agrochemicals to use pesticidal compounds to use novel pesticidal compounds in order to avoid or to fight the development of resistant strains to the active ingredients used by the farmer.

We have now found a new family of compounds which possess the above mentioned characteristics.

Accordingly, the present invention relates to a heterocyclylethylbenzamide derivative of general formula (I)

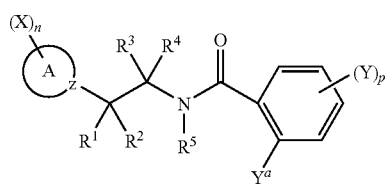

in which:
n is 1, 2, 3, 4 or 5;
p is 1, 2, 3 or 4;
A represents a 6-membered non-fused heterocycle with one, two or three heteroatoms which may be the same or different, provided that A is different from pyridyl, piperidine and piperazine;
z is a carbon atom or a heteroatom which can not be substituted by X;
X is the same or different and is a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a $C_1$-$C_8$-halogenoalkyl having 1 to 5 halogen atoms, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)$C_1$-$C_6$-alkyl, a ($C_1$-$C_6$-alkynyloxyimino)-$C_1$-$C_6$-alkyl, a benzyloxyimino)-$C_1$-$C_6$-alkyl, a benzyloxy, a benzylsulfanyl, a benzylamino, a phenoxy, a phenylsulfanyl a phenyl or a phenylamino;

$R^1$ and $R^2$ are the same or different and are a hydrogen atom, a hydrogen atom, a cyano group, a formyl group, a carboxy group, a carbamoyl group, a (hydroxyimino)-$C_1$-$C_6$-alkyl group, a $C_1$-$C_8$-alkyl, $C_3$-$C_7$-cycloalkyl-$C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-halogenoalkyl having 1 to 5 halogen atoms, a $C_1$-$C_8$-alkylcarbamoyl, a di-$C_1$-$C_8$-alkylcarbamoyl, a $C_1$-$C_8$-alkoxycarbamoyl, a $C_1$-$C_8$-alkoxycarbonyl or a $C_1$-$C_8$-halogenoalkoxycarbonyl having 1 to 5 halogen atoms;

$R^3$ and $R^4$ are the same or different and are a hydrogen atom, a cyano group, a formyl group, a carboxy group, a carbamoyl group, a (hydroxyimino)-$C_1$-$C_6$-alkyl group, a $C_1$-$C_8$-alkyl, a $C_3$-$C_7$-cycloalkyl-$C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_9$-halogenoalkyl having 1 to 5 halogen atoms, a $C_1$-$C_8$-alkylcarbamoyl, a di-$C_1$-$C_8$-alkylcarbamoyl, a $C_1$-$C_8$-alkoxycarbamoyl, a $C_1$-$C_8$-alkoxycarbonyl or a $C_1$-$C_8$-halogenoalkoxycarbonyl having 1 to 5 halogen atoms;

$R^5$ is a hydrogen atom, a $C_1$-$C_6$-alkyl, or a $C_3$-$C_7$-cycloalkyl;

Y is the same or different and is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_9$-alkyl, a $C_2$-$C_8$-alkenyl, a $C_2$-$C_8$-alkynyl, a $C_1$-$C_8$-alkoxy, a $C_1$-$C_8$-halogenoalkyl having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)$C_1$-$C_6$-alkyl, a ($C_1$-$C_6$-alkynyloxyimino)-$C_1$-$C_6$-alkyl, a (benzyloxyimino)-$C_1$-$C_6$-alkyl; and $Y^a$ is a halogen atom, a cyano group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkoxy, a $C_1$-$C_8$-halogenoalkyl having 1 to 5 halogen atoms, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_9$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkyl-sulphonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl;

as well as its salts, N-oxydes, metallic complexes, metalloidic complexes and optically active isomers.

In the context of the present invention:
halogen means fluorine, bromine, chlorine or iodine.
carboxy means —C(=O)OH; carbonyl means —C(=O)—; carbamoyl means —C(=O)NH$_2$; N-hydroxycarbamoyl means —C(=O)NHOH;
an alkyl group, an alkenyl group, and an alkynyl group as well as moieties containing these terms, can be linear or branched; and
heteroatom means sulphur, nitrogen or oxygen.

In the context of the present invention, it has also to be understood that in the case of di-substituted amino and of di-substituted carbamoyl radicals, the two substituents may form together with the nitrogen atom bearing them a saturated heterocyclic ring containing 3 to 7 atoms.

Any of the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of general formula (I) wherein X represents a hydroxy, a sulfanyl group or an amino group may be found in its tautomeric form resulting from the shift of the proton of said hydroxy, sulfanyl or amino group. Such tautomeric forms of such compounds are also part of the present invention. More generally speaking, all tautomeric forms of compounds of general formula (I) wherein X represents a hydroxy, a sulfanyl group or an amino group, as well as the tautomeric forms of the compounds which can optionally be used as intermediates in the preparation processes, and which will be defined in the description of these processes, are also part of the present invention.

According to the present invention, the "A" group may be substituted in any position by $(X)_n$, in which X and n are as defined above. Preferably, the present invention relates to heterocyclylethylbenzamide derivative of general formula (I) in which the different characteristics may be chosen alone or in combination as being:
as regards n, n is 1 or 2;
as regards X, X is chosen as being a methyl group, a halogen atom or $C_1$-$C_8$-halogenoalkyl having 1 to 5 halogen atoms. More preferably, X is a halogen atom.

According to the present invention, the carbon atoms of the carboxamide moiety of the compound of formula (I) are substituted by $R^1$, $R^2$, $R^3$ and $R^4$; $R^1$, $R^2$, $R^3$ and $R^4$ being as defined above. Preferably, the present invention also relates to heterocyclylethylbenzamide derivative of general formula (I) in which the different characteristics may be chosen alone or in combination as being:
as regards $R^1$ and $R^2$, $R^1$ and $R^2$ are chosen, independently of each other, as being a hydrogen atom, a $C_1$-$C_8$-alkyl, a $C_2$-$C_8$-alkenyl, a $C_2$-$C_8$-alkynyl, a $C_3$-$C_8$-cycloalkyl, a $C_3$-$C_7$-cycloalkyl-$C_1$-$C_8$-alkyl, a $C_3$-$C_8$-halogenocycloalkyl having 1 to 5 halogen atoms or a $C_1$-$C_8$-halogenoalkyl having 1 to 5 halogen atoms;
as regards $R^3$ and $R^4$, $R^3$ and $R^4$ are chosen, independently of each other, as being a hydrogen atom, a $C_1$-$C_8$-alkyl, a $C_2$-$C_8$-alkenyl, a $C_2$-$C_8$-alkynyl, a $C_3$-$C_8$-cycloalkyl, a $C_3$-$C_7$-cycloalkyl-$C_1$-$C_8$-alkyl, a $C_3$-$C_8$-halogenocycloalkyl having 1 to 5 halogen atoms or a $C_1$-$C_8$-halogenoalkyl having 1 to 5 halogen atoms.

According to the present invention, the nitrogen atom of the carboxamide moiety of the compound of formula (I) is substituted by $R^5$, $R^5$ being a hydrogen atom, a $C_1$-$C_6$-alkyl or a $C_3$-$C_7$-cycloalkyl. Preferably, the $C_3$-$C_7$-cycloalkyl is cyclopropyl.

According to the present invention, the phenyl moiety is substituted in ortho position by $Y^a$ and may be substituted in any other position by $(Y)_p$, in which $Y^a$, Y and p are as defined above. Preferably, the present invention relates to heterocyclylethylbenzamide derivative of general formula (I) in which the different characteristics may be chosen alone or in combination as being:

as regards $Y^a$, $Y^a$ is chosen as being a halogen atom, a pentafluoro-$\lambda^6$-sulfanyl group, a $C_1$-$C_8$-alkyl, a $C_1$-$C_8$-halogenoalkyl having 1 to 5 halogen atoms or a $C_1$-$C_8$-halogenoalkoxy having 1 to 5 halogen atoms;

as regards p, p is 1;

as regards Y, Y is chosen as being a hydrogen atom or a halogen atom. More preferably Y is a hydrogen atom.

According to the present invention, the "A" group of the compound of general formula (I) is a six membered ring non-fused heterocycle with one, two or three heteroatoms which may be the same or different. Preferably, the present invention also relates to heterocyclylethylbenzamide derivative of general formula (I) in which the different characteristics may be chosen alone or in combination as being:

A is chosen as being a pyridazine, a pyriidine or a pyrazine. More preferably, A is a pyrimidine;

A is substituted in ortho position.

Specific examples of "A" group include:

A represents a heterocycle of the general formula (A-1)

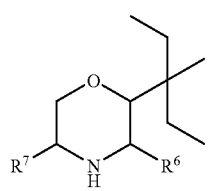
(A-1)

in which:
R⁶ may be a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms or a $C_1$-$C_4$-halogenoalkoxy having 1 to 5 halogen atoms;

R⁷ may be a hydrogen atom, a $C_1$-$C_4$-alkyl, a $C_1$-$C_4$-halogenoalkyl having 1 to 5 halogen atoms or a benzyl.

A represents a heterocycle of the general formula (A-2)

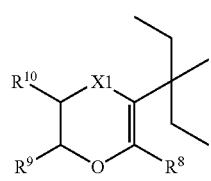
(A-2)

in which:
$X^1$ may be a sulphur atom, —SO—, —SO₂— or —CH₂—;

R⁵ may be a $C_1$-$C_4$-alkyl or a $C_1$-$C_4$-halogenoalkyl having 1 to 5 halogen atoms; and R⁹ and R¹⁰ may be the same or different and may be a hydrogen atom or a $C_1$-$C_4$-alkyl.

A represents a heterocycle of the general formula (A-3)

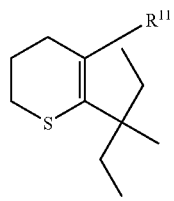
(A-3)

in which:
R¹¹ may be a $C_1$-$C_4$-alkyl or a $C_1$-$C_4$-halogenoalkyl having 1 to 5 halogen atoms;

A represents a heterocycle of the general formula (A-4)

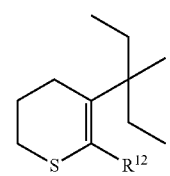
(A-4)

in which:
R¹² may be a $C_1$-$C_4$-alkyl or a $C_1$-$C_4$-halogenoalkyl having 1 to 5 halogen atoms.

A represents a heterocycle of the general formula (A-5)

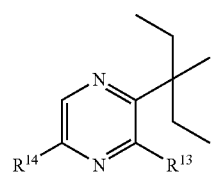
(A-5)

in which:
R¹³ may be a hydrogen atom, a halogen atom, a $C_1$-$C_4$-alkyl or a $C_1$-$C_4$-halogenoalkyl having 1 to 5 halogen atoms; and R¹⁴ may be a halogen atom, a $C_1$-$C_4$-alkyl or a $C_1$-$C_4$-halogenoalkyl having 1 to 5 halogen atoms.

A represents a heterocycle of the general formula (A-6)

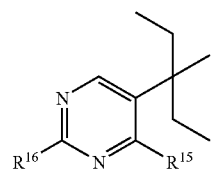
(A-6)

in which:
R¹⁵ may be a hydrogen atom, a halogen atom, a $C_1$-$C_4$-alkyl or a $C_1$-$C_4$-halogenoalkyl having 1 to 5 halogen atoms; and R¹⁶ may be, a halogen atom, a $C_1$-$C_4$-alkyl or a $C_1$-$C_4$-halogenoalkyl having 1 to 5 halogen atoms.

A represents a heterocycle of the general formula (A-7)

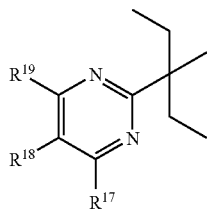
(A-7)

in which:
$R^{17}$ and $R^{19}$ may be the same or different and may be a hydrogen atom, a halogen atom, a $C_1$-$C_4$-alkyl or a $C_1$-$C_4$-halogenoalkyl having 1 to 5 halogen atoms; and
$R^{18}$ may be a halogen atom, a $C_1$-$C_4$-alkyl or a $C_1$-$C_4$-halogenoalkyl having 1 to 5 halogen atoms.

A represents a heterocycle of the general formula (A-8)

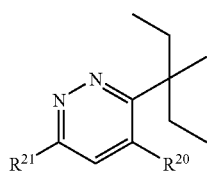
(A-8)

in which:
$R^{20}$ may be a hydrogen atom, a halogen atom, a $C_1$-$C_4$-alkyl or a $C_1$-$C_4$-halogenoalkyl having 1 to 5 halogen atoms; and
$R^{21}$ may be a halogen atom, a $C_1$-$C_4$-alkyl or a $C_1$-$C_4$-halogenoalkyl having 1 to 5 halogen atoms.

A represents a heterocycle of the general formula (A-9)

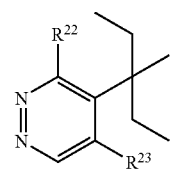
(A-9)

in which:
$R^{22}$ may be a hydrogen atom, a halogen atom, a $C_1$-$C_4$-alkyl or a $C_1$-$C_4$-halogenoalkyl having 1 to 5 halogen atoms; and
$R^{23}$ may be, a halogen atom, a $C_1$-$C_4$-alkyl or a $C_1$-$C_4$-halogenoalkyl having 1 to 5 halogen atoms The present invention also relates to a process for the preparation of the compound of general formula (I). Thus, according to a further aspect of the present invention there is provided a process for the preparation of compound of general formula (I) as defined above, which comprises reacting a heterocyclyl-ethylamine derivative of general formula (II) or one of its salt:

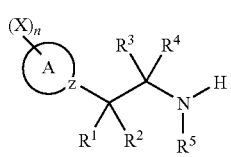
(II)

in which A, X, n, z, $R^1$, $R^2$, $R^3$, $R^4$ and $R^5$ are as defined above;
with a carboxylic acid derivative of the general formula (III)

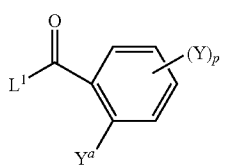
(III)

in which:
$Y^a$, Y and p are as defined above; and
L' is a leaving group chosen as being a halogen atom, a hydroxyl group, —$OR^{24}$, —$OCOR^{24}$, $R^{24}$ being a $C_1$-$C_6$ alkyl, a $C_1$-$C_6$ haloalkyl, a benzyl, 4-methoxybenzyl, pentafluorophenyl, and a group of formula:

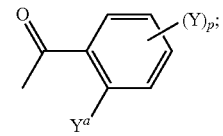

in the presence of a catalyst and, if L¹ is a hydroxyl group, in the presence of a condensing agent.

The process according to the present invention is conducted in the presence of a catalyst. Suitable catalyst may be chosen as being 4-dimethyl-aminopyridine, 1-hydroxy-benzotriazole or dimethylformamide.

In case L¹ is a hydroxy group, the process according to the present invention is conducted in the presence of condensing agent. Suitable condensing agent may be chosen as being acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl-chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromo-tripyrrolidino-phosphonium-hexafluorophosphate.

When $R^5$ is a hydrogen atom, the above mentioned process for the preparation of compound of general formula (I) may optionally be completed by a further step according to the following reaction scheme:

a second step according to reaction scheme A-2:

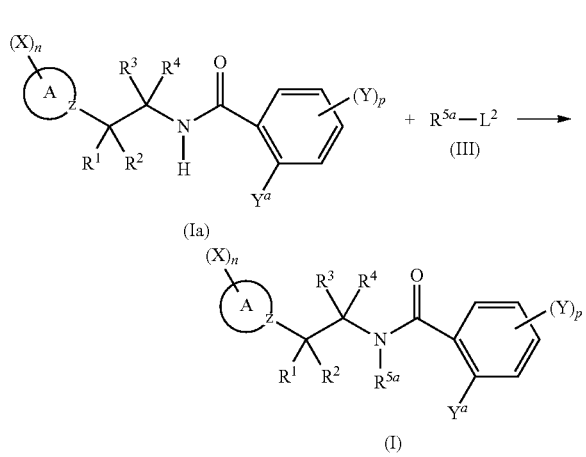

(Ia)

(I)

in which:
A, X, n, z, R$^1$, R$^2$, R$^3$, R$^4$, Y$^a$, Y and p are as defined above;
R$^{5a}$ is a C$_1$-C$_6$-alkyl, or a C$_3$-C$_7$-cycloalkyl; and
L$^2$ is a leaving group chosen as being a halogen atom, a 4-methyl phenylsulfonyloxy or a methylsulfonyloxy;
comprising the reaction of a compound of general formula (Ia) with a compound of general formula (III) to provide a compound of general formula (I).

Depending on the definition of R$^1$, R$^2$, R$^3$, R$^4$ or R$^5$, amine derivatives of general formula (II) may be prepared by different processes. One example (A) of such a process may be when:
A, z, X, n are as defined above; and
R$^1$ and R$^2$ are independently chosen as being a C$_1$-C$_6$ alkyl or a C$_3$-C$_7$ cycloalkyl-C$_1$-C$_6$ alkyl
R$^3$, R$^4$ and R$^5$ are hydrogen atoms;
then, the amine derivative of general formula (H) may be prepared according to a process which comprises:
a first step according to reaction scheme A-1:

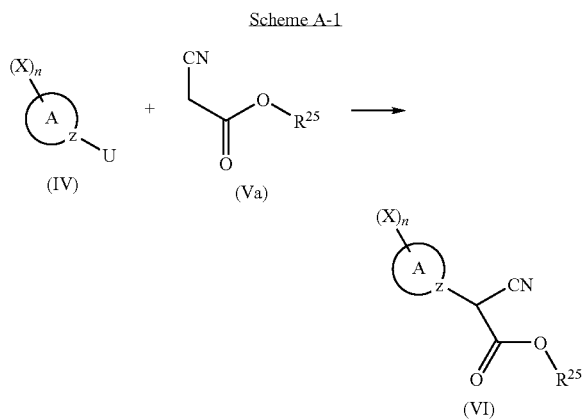

in which:
A, z, X and n are as defined above;
R$^{25}$ is a C$_1$-C$_6$ alkyl, a C$_1$-C$_6$ haloalkyl, a benzyl, 4-methoxybenzyl or pentafluorophenyl;
U is a leaving group chosen as being a halogen, a C$_1$-C$_6$ alkylsulfonate or a C$_1$-C$_6$ haloalkylsulfonate; comprising the arylation of a cyanoacetate derivative of general formula (Va) by a heterocylic derivative of general formula (IV), to provide a heterocyclyl-cyanoacetate derivative of general formula (VI), in the presence of a base, at a temperature of from 0° C. to 200° C.;

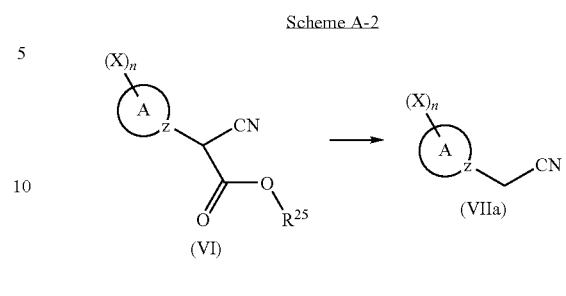

in which:
A, z, X and n are as defined above;
R$^{25}$ is a C$_1$-C$_6$ alkyl, a C$_1$-C$_6$ haloalkyl, a benzyl, 4-methoxybenzyl or pentafluorophenyl;
comprising a basic hydrolysis, an acidic hydrolysis or a displacement by an halide of a compound of general formula (VI) in the same or a different pot to provide, upon heating at a temperature of from 40° C. to reflux, a heterocylclyl-acetonitrile derivative of general formula (VIIa);
a third step according to reaction scheme A-3

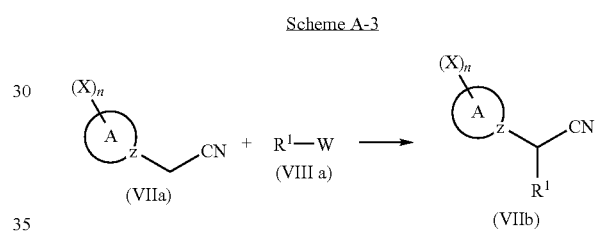

in which:
A, z, X and n are as defined above;
R$^1$ is a C$_1$-C$_6$ alkyl or a C$_3$-C$_7$ cycloalkyl-C$_1$-C$_6$ alkyl,
W is a halogen atom, a C$_1$-C$_6$ alkylsulfonate, a C$_1$-C$_6$ haloalkylsulfonate or a 4-methyl-phenylsulfonate;
comprising the alkylation of a compound of general formula (VII a) by a reagent of general formula (VIII a) to provide a compound of general formula (VII b);
a fourth step according to reaction scheme A-4:

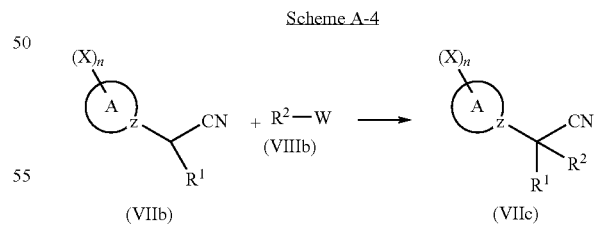

in which:
A, z, X and n are as defined above;
R$^1$, R$^2$ are a C$_1$-C$_6$ alkyl or a C$_3$-C$_7$ cycloalkyl-C$_1$-C$_6$ alkyl,
W is a halogen atom, a C$_1$-C$_6$ alkylsulfonate, a C$_1$-C$_6$ haloalkylsulfonate or a 4-methyl-phenylsulfonate;
comprising the alkylation of a compound of general formula (VII b) by a reagent of general formula (VIIIb) to provide a compound of general formula (VIIc);

a fifth step according to reaction scheme A-5

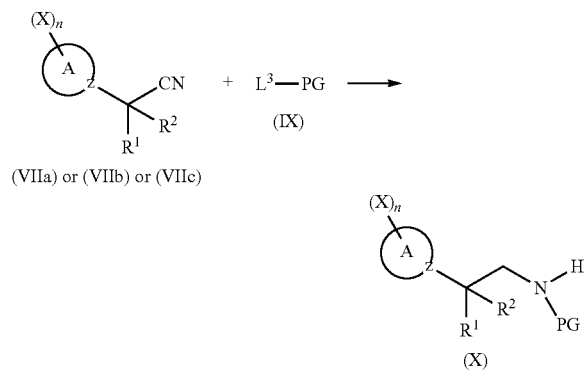

in which:
A, z, X and n are as defined above;
R$^1$, R$^2$ are a hydrogen atom, a C$_1$-C$_6$ alkyl or a C$_3$-C$_7$ cycloalkyl-C$_1$-C$_6$ alkyl,
L$^3$ is a leaving group chosen as being a —OR$^{26}$ group or a —OCOR$^{26}$ group, R$^{26}$ being a C$_1$-C$_6$ alkyl, a C$_1$-C$_6$ haloalkyl, a benzyl, 4-methoxybenzyl or pentafluorophenyl;
PG represents a protecting group which may be a —COOR$^{27}$ group or —COR$^{27}$ group, R$^{27}$ being a C$_1$-C$_6$ alkyl, a C$_1$-C$_6$ haloalkyl, a benzyl, 4-methoxybenzyl or pentafluorophenyl;
comprising the reduction, by hydrogenation or by an hydride donor, of a compound of general formula (VIIa), (VIIb) or (VIIc), in the presence of a catalyst and in the presence of a compound of general formula (IX) to produce a compound of general formula (X), at a temperature of from 0° C. to 150° C. and under a pressure of from 1 bar and 100 bar, a sixth step according to reaction scheme A-6:

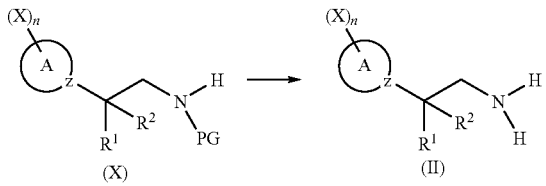

in which:
A, z, X and n are as defined above;
R$^1$, R$^2$ are a hydrogen atom, a C$_1$-C$_6$ alkyl or a C$_3$-C$_7$ cycloalkyl-C$_1$-C$_6$ alkyl,
PG represents a protecting group which may be a —COOR$^{28}$ group or —COR$^{28}$ group, R$^{28}$ being a C$_1$-C$_6$ alkyl, a C$_1$-C$_6$ haloalkyl, a benzyl, 4-methoxybenzyl or pentafluorophenyl;
comprising a deprotection reaction, in an acidic or in a basic medium, of a compound of general formula (X) to provide an amine derivative of general formula (II) or one of its salt.

The first step (step A-1) is conducted in the presence of a base. Preferably, the base will be chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

The first step (step A-1) according to the present invention is conducted at a temperature of from 0° C. to 200° C. Preferably, first step (step A-1) is conducted at a temperature of from 0° C. to 120° C., more preferably at a temperature of from 0° C. to 80° C.

The first step (step A-1) according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step A-1) according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(–)-1-[(S)-2-(dicyclohexylphosphino)ferrocenyl]ethyldicyclohexylphosphine and its corresponding enantiomer, or a mixture of both; (R)-(–)-1[(S)-2-(dicyclohexylphosphino)ferrocenyl]ethyldiphenylphosphine and its corresponding enantiomer, or a mixture of both; (R)-(–)-1[(S)-2-(diphenylphosphino)ferrocenyl]ethyldi-t-butylphosphine and its corresponding enantiomer, or a mixture of both; or (R)-(–)-1[(S)-2-(diphenylphosphino)ferrocenyl]ethyldicyclohexylphosphine and its corresponding enantiomer, or a mixture of both.

The fifth step (step A-5) according to the present invention is conducted in the presence of a hydride donor. Preferably, the hydride donor is chosen as being metal or metalloid hydrides such as LiAlH$_4$, NaBH$_4$, KBH$_4$, B$_2$H$_6$.

The fifth step (step A-5) according to the present invention is conducted in the presence of a catalyst. Preferably, the catalyst is chosen as being Co(II)-Chloride, Ni(II)-chloride, ammonia or one of its salt, Palladium on charcoal, Raney Nickel, Raney Cobalt or Platinum.

The fifth step (step A-5)) according to the present invention is conducted at a temperature of from 0° C. to 150° C. Preferably the temperature is of from 10° C. to 120° C. More preferably, the temperature is of from 10° C. to 80° C.

The fifth step (step A-5) according to the present invention is conducted under a pressure of from 1 bar to 100 bar. Preferably the pressure is of from 1 bar to 50 bar.

The fifth step (step A-5) according to the present invention may be conducted in the presence of an organic solvent, of water or of a mixture thereof. Preferably, the solvent is chosen as being ether, alcohol, carboxylic acid, or a mixture thereof with water or pure water.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesise.

On the basis of his general knowledge and of available publications, the skilled worker will also be able to prepare intermediate compound of formula (V) according to the present invention.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous. Examples of suitable fungicide mixing partners may be selected in the following lists:

1) a compound capable to inhibit the nucleic acid synthesis like benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid;

2) a compound capable to inhibit the mitosis and cell division like benomyl, carbendazim, diethofencarb, ethaboxam, fuberidazole, pencycuron, thiabendazole thiophanate-methyl, zoxamide;

3) a compound capable to inhibit the respiration for example as CI-respiration inhibitor like diflumetorim;

as CII-respiration inhibitor like boscalid, carboxin, fenfuram, flutolanil, furametpyr, furmecyclox, mepronil, oxycarboxine, penthiopyrad, thifluzamide;

as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

4) a compound capable of to act as an uncoupler like dinocap, fluazinam, meptyldinocap;

5) a compound capable to inhibit ATP production like fentin acetate, fentin chloride, fentin hydroxide, silthiofam;

6) a compound capable to inhibit AA and protein biosynthesis like andoprim, blasticidin-S, cyprodinil, kasugamycin, kasugamycin hydrochloride hydrate, mepanipyrim, pyrimethanil;

7) a compound capable to inhibit the signal transduction like fenpiclonil, fludioxonil, quinoxyfen;

8) a compound capable to inhibit lipid and membrane synthesis like biphenyl, chlozolinate, edifenphos, iodocarb, iprobenfos, iprodione, isoprothiolane, procymidone, propamocarb, propamocarb hydrochloride, pyrazophos, tolclofos-methyl, vinclozolin;

9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

10) a compound capable to inhibit cell wall synthesis like benthiavalicarb, bialaphos, dimethomorph, flumorph, iprovalicarb, polyoxins, polyoxorim, validamycin A;

11) a compound capable to inhibit melanine biosynthesis like carpropamid, diclocymet, fenoxanil, phthalide, pyroquilon, tricyclazole;

12) a compound capable to induce a host defence like acibenzolar-S-methyl, probenazole, tiadinil;

13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, man-copper, mancozeb, maneb, metiram, metiram zinc, oxine-copper, propineb, sulphur and sulphur preparations including calcium polysulphide, thiram, tolylfluanid, zineb, ziram;

14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl 1H-imidazole-1-carboxylate, 2-(4-chlorophenyl)-N-{2-[3-methoxy-4-(prop-2-yn-1-yloxy)phenyl]ethyl}-2-(prop-2-yn-1-yloxy)acetamide, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3,4,5-trichloropyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidin-7-amine, 5-chloro-7-(4-methylpiperidin-1-yl)-6-(2,4,6-trifluorophenyl)[1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidin-7-amine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, methasulfocarb, methyl (2-chloro-5-{(1E)-N-[(6-methylpyridin-2-yl)methoxy]ethanimidoyl}benzyl)carbamate, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl 3-(4-chlorophenyl)-3-{[N-(isopropoxycarbonyl)valyl]amino}propanoate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-N$^2$-(methylsulfonyl)valinamide, N-{(Z)-[(cyclopropylmethoxy)imino][6-(difluoromethoxy)-2,3-difluorophenyl]methy}-2-phenylacetamide, N-{2-[3-chloro-5-(trifluoromethyl)pyridin-2-yl]ethyl}-2-(trifluoromethyl)benzamide, natamycin, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyrrolnitrine, quintozene, tecloftalam, tecnazene, triazoxide, trichlamide and zarilamid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The fungicidal compositions of the present invention can be used to curatively or preventively control the phytopathogenic fungi of crops. Thus, according to a further aspect of the present invention, there is provided a method for curatively or preventively controlling the phytopathogenic fingi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the present invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the present invention, mention may be made of:

Powdery mildew diseases such as:

*Blumeria* diseases, caused for example by *Blumeria graminis;*

*Podosphaera* diseases, caused for example by *Podosphaera leucotricha;*

*Sphaerotheca* diseases, caused for example by *Sphaerotheca fuliginea;*

Uncinula diseases, caused for example by *Uncinula necator*;
Rust diseases such as:
  *Gymnosporangium* diseases, caused for example by *Gymnosporangium sabinae*;
  *Hemileia* diseases, caused for example by *Hemileia vastatrix*;
  *Phakopsora* diseases, caused for example by *Phakopsora pachyrhizi* or *Phakopsora meibomiae*;
  *Puccinia* diseases, caused for example by *Puccinia recondita*;
  *Uromyces* diseases, caused for example by *Uromyces appendiculatus*; Oomycete diseases such as:
  *Bremia* diseases, caused for example by *Bremia lactucae*;
  *Peronospora* diseases, caused for example by *Peronospora pisi* or *P. brassicae*;
  *Phytophthora* diseases, caused for example by *Phytophthora infestans*;
  *Plasmopara* diseases, caused for example by *Plasmopara viticola*;
  *Pseudoperonospora* diseases, caused for example by *Pseudoperonospora humuli* or *Pseudoperonospora cubensis*;
  *Pythium* diseases, caused for example by *Pythium ultimum*;
Leafspot, leaf blotch and leaf blight diseases such as:
  *Alternaria* diseases, caused for example by *Alternaria solani*;
  *Cercospora* diseases, caused for example by *Cercospora beticola*;
  *Cladiosporum* diseases, caused for example by *Cladiosporium cucumerinum*;
  *Cochliobolus* diseases, caused for example by *Cochliobolus sativus*;
  *Colletotrichum* diseases, caused for example by *Colletotrichum lindemuthanium*;
  *Cycloconium* diseases, caused for example by *Cycloconium oleaginum*;
  *Diaporthe* diseases, caused for example by *Diaporthe citri*;
  *Elsinoe* diseases, caused for example by *Elsinoe fawcettii*;
  *Gloeosporium* diseases, caused for example by *Gloeosporium laeticolor*;
  *Glomerella* diseases, caused for example by *Glomerella cingulata*;
  *Guignardia* diseases, caused for example by *Guignardia bidwelli*;
  *Leptosphaeria* diseases, caused for example by *Leptosphaeria maculans*; *Leptosphaeria nodorum*;
  *Magnaporthe* diseases, caused for example by *Magnaporthe grisea*;
  *Mycosphaerella* diseases, caused for example by *Mycosphaerella graminicola*; *Mycosphaerella arachidicola*; *Mycosphaerella fijiensis*;
  *Phaeosphaeria* diseases, caused for example by *Phaeosphaeria nodorum*;
  *Pyrenophora* diseases, caused for example by *Pyrenophora teres*;
  *Ramularia* diseases, caused for example by *Ramularia collo-cygni*;
  *Rhynchosporium* diseases, caused for example by *Rhynchosporium secalis*;
  *Septoria* diseases, caused for example by *Septoria apii* or *Septoria lycopercisi*;
  *Typhula* diseases, caused for example by *Typhula incarnata*;
  *Venturia* diseases, caused for example by *Venturia inaequalis*;
Root and stem diseases such as:
  *Corticium* diseases, caused for example by *Corticium graminearum*;
  *Fusarium* diseases, caused for example by *Fusarium oxysporum*;
  *Gaeumannomyces* diseases, caused for example by *Gaeumannomyces graminis*;
  *Rhizoctonia* diseases, caused for example by *Rhizoctonia solani*;
  *Tapesia* diseases, caused for example by *Tapesia acuformis*;
  *Thielaviopsis* diseases, caused for example by *Thielaviopsis basicola*;
Ear and panicle diseases such as:
  *Alternaria* diseases, caused for example by *Alternaria* spp.;
  *Aspergillus* diseases, caused for example by *Aspergillus flavus*;
  *Cladosporium* diseases, caused for example by *Cladosporium* spp.;
  *Claviceps* diseases, caused for example by *Claviceps purpurea*;
  *Fusarium* diseases, caused for example by *Fusarium culmorum*;
  *Gibberella* diseases, caused for example by *Gibberella zeae*;
  *Monographella* diseases, caused for example by *Monographella nivalis*;
Smut and bunt diseases such as:
  *Sphacelotheca* diseases, caused for example by *Sphacelotheca reiliana*;
  *Tilletia* diseases, caused for example by *Tilletia caries*;
  *Urocystis* diseases, caused for example by *Urocystis occulta*;
  *Ustilago* diseases, caused for example by *Ustilago nuda*;
Fruit rot and mould diseases such as:
  *Aspergillus* diseases, caused for example by *Aspergillus flavus*;
  *Botrytis* diseases, caused for example by *Botrytis cinerea*;
  *Penicillium* diseases, caused for example by *Penicillium expansum*;
  *Sclerotinia* diseases, caused for example by *Sclerotinia sclerotiorum*;
  *Verticilium* diseases, caused for example by *Verticilium alboatrum*;
Seed and soilborne decay, mould, wilt, rot and damping-off diseases:
  *Fusarium* diseases, caused for example by *Fusarium culmorum*;
  *Phytophthora* diseases, caused for example by *Phytophthora cactorum*;
  *Pythium* diseases, caused for example by *Pythium ultimum*;
  *Rhizoctonia* diseases, caused for example by *Rhizoctonia solani*;
  *Sclerotium* diseases, caused for example by *Sclerotium rolfsii*;
  *Microdochium* diseases, caused for example by *Microdochium nivale*;
Canker, broom and dieback diseases such as:
  *Nectria* diseases, caused for example by *Nectria galligena*;
Blight diseases such as:
  *Monilinia* diseases, caused for example by *Monilinia laxa*;
Leaf blister or leaf curl diseases such as:

*Taphrina* diseases, caused for example by *Taphrina deformans*;

Decline diseases of wooden plants such as:

Esca diseases, caused for example by *Phaemoniella clamydospora*;

Diseases of flowers and Seeds such as:

*Botrytis* diseases, caused for example by *Botrytis cinerea*;

Diseases of tubers such as:

*Rhizoctonia* diseases, caused for example by *Rhizoctonia solani*.

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, *trichophyton* diseases and candidiases or diseases caused by *Aspergillus* spp., for example *Aspergillus fumigatus*.

The aspects of the present invention will now be illustrated with reference to the following tables of compounds and examples. The following Table illustrates in a non-limiting manner examples of fungicidal compounds according to the present invention. In the following Examples, M+1 (or M−1) means the molecular ion peak, plus or minus 1 a.m.u. (atomic mass units) respectively, as observed in mass spectroscopy and M (ApcI+) means the molecular ion peak as it was found via positive atmospheric pressure chemical ionisation in mass spectroscopy.

TABLE A

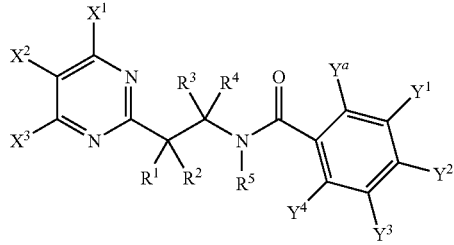

| Compound | $X^1$ | $X^2$ | $X^3$ | $Y^a$ | $Y^1$ | $Y^2$ | $Y^3$ | $Y^4$ | $R^1$ | $R^2$ | $R^3$ | $R^4$ | $R^5$ | M + 1 |
|---|---|---|---|---|---|---|---|---|---|---|---|---|---|---|
| A-1 | H | Br | H | $CF_3$ | H | H | H | H | H | H | H | H | H | 374 |

TABLE B

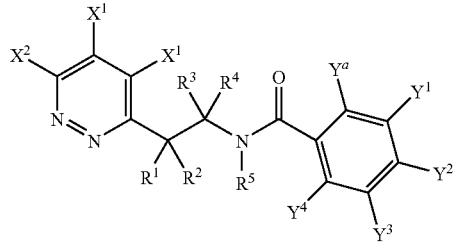

| Compound | $X^1$ | $X^2$ | $X^3$ | $Y^a$ | $Y^1$ | $Y^2$ | $Y^3$ | $Y^4$ | $R^1$ | $R^2$ | $R^3$ | $R^4$ | $R^5$ | M + 1 |
|---|---|---|---|---|---|---|---|---|---|---|---|---|---|---|
| B-1 | H | H | Cl | $CF_3$ | H | H | H | H | H | H | H | H | H | 330 |

TABLE C

| Compound | X¹ | X² | X³ | $Y^a$ | Y¹ | Y² | Y³ | Y⁴ | R¹ | R² | R³ | R⁴ | R⁵ | M + 1 |
|---|---|---|---|---|---|---|---|---|---|---|---|---|---|---|
| C-1 | H | H | Cl | CF₃ | H | H | H | H | H | H | H | H | H | 330 |

EXAMPLES OF PROCESS FOR THE PREPARATION OF THE COMPOUND OF GENERAL FORMULA (I)

Synthesis of N-[2-(5-bromopyrimidin-2-yl)ethyl]-2-(trifluoromethyl)benzamide (Compound A-1)

Synthesis of ethyl (5-bromopyrimidin-2-yl)(cyano)acetate

To a chilled stirred suspension of sodium hydride (60% in oil, 34.55 mmol) in tetrahydrofuran (20 mL) was added 1.17 g of ethyl cyanoacetate (10.34 mmol) portionwise over 10 minutes. After effervescence has ceased, the yellow cloudy mixture was left to warm up to room temperature whilst stirring. 2.00 g of 5-bromo,2-bromo-pyrimidine (10.34 mmol) in 30 mL of tetrahydrofuran was added. And the mixture was left to stir at room temperature for six hours. The resultant brown mixture was concentrated under reduced pressure to give a bright brown precipitate to which water (200 mL) was added. After extraction with heptane (200 mL), the aqueous phase was acidified by the addition of HCl 1M and the resultant precipitate was collected by filtration to give on drying ethyl (5-bromopyrimidin-2-yl)(cyano)acetate as a bright brown powder (0.67 g, yield=24%).

¹H NMR δ (ppm, DMSO-d₆): 3.5 (b, 1H); 8.9 (b, 1H); 8.45 (b, 1H); 4.24 (t, 2H); 1.25 (t, 3H).

Synthesis of (5-bromopyrimidin-2-yl)acetonitrile

To 2.70 g of ethyl (5-bromopyrimidin-2-yl)(cyano)acetate (9.970 mmol) in dimethylsulfoxyde (20 ml) was added 0.584 g of sodium chloride (9.970 mmol) and 0.18 mL of water (9.970 mmol). The mixture was heated at 120° C. under a nitrogen atmosphere for 3 hours. The mixture was poured into water (300 mL) and the resultant precipitate was collected by filtration to give 5-bromopyrimidin-2-yl)acetonitrile (0.6 g, yield=30%).

The clear yellow filtrate was salted by the addition of a saturated solution of sodium chloride, neutralided with sodium hydroxide, to give a red solution which was then extracted with dichloromethane. The organic phase was collected, dried over magnesium sulphate, and evaporated in vacuo to give a dark oil, which was purified by flash chromatography using 2/1 heptane/ethyl acetate as eluent, yielding to 5-bromopyrimidin-2-yl)acetonitrile (0.9 g, yield=43%).

¹H NMR δ (ppm, CDCl₃): 9.0 (s, 2H); 4.25 (s, 2H).

Synthesis of tert-butyl [2-(5-bromopyrimidin-2-yl)ethyl]carbamate

To a cold (−5° C. to 0° C.), stirred mixture of the 5-bromopyrimidin-2-yl)acetonitrile (0.9 g), tert-butyloxy-carbonate (1.98 g; 2 equivalents), and nickel chloride hexahydrate (1.08 g) under a nitrogen atmosphere was added, portionwise, sodium borohydride (0.86 g; 5 equivalents). After the addition the mixture was left to stir, whilst warming to room temperature, for 6 hrs and left to stand overnight.

The mixture was diluted with ethyl acetate (200 mls) and filtered through kieselghur. The filtrate was washed with brine and the organic phase was collected, dried over MgSO₄, and evaporated in vacuo to give the product as a brown oil. Yield: 0.6 g The crude product was purified by flash chromatography to yield to 0.22 g of tert-butyl [2-(5-bromopyrimidin-2-yl)ethyl] carbamate (16%)

¹H NMR δ (CDCl₃): 8.76 (s, 2H); 5.22 (b, NH); 3.64 (m, 2H); 3.13 (m, 2H); 1.43 (s, 9H).

Synthesis of N-[2-(5-bromopyrimidin-2-yl)ethyl]-2-(trifluoromethyl)benzamide (Compound 1)

To a clear pale yellow mixture of the tert-butyl [2-(5-bromopyrimidin-2-yl)ethyl]carbamate (0.22 g, 0.7 mmol) in dichloromethane (2 ml) was added trifluoroacetic acid (10 equivs) and the mixture was left to stir at room temperature for 7 hrs and left to stand overnight. Saturated sodium bicarbonate solution was added until the effervescence stopped (to give a basic medium). The organic phase was collected, dried over MgSO4, and evaporated in vacuo after filtration, to yield to 0.12 g of 2-(5-bromopyrimidin-2-yl)ethanamine (80%) which is used directly without purification.

To 0.06 g of 2-(5-bromopyrimidin-2-yl)ethanamine (3.0 mmol) and triethylamine (0.03 g, 1.0 equivalent) in THF (5 ml), at room temperature whilst stirring, was added the 2-trifluoromethyl benzoyl chloride (0.062 g, 1.0 equivalent) and the mixture was left to stir at room temperature overnight. The solvent was removed by evaporation in vacuo and saturated sodium bicarbonate (10 mls) was added. The mixture was extracted with dichloromethane and the organic phase was collected, dried over MgSO₄, and evaporated in vacuo to give the crude product which was purified by chromatography on silica using 1:1 heptane/ethyl acetate to yield to 0.036 g of N-[2-(5-bromopyrimidin-2-yl)ethyl]-2-(trifluoromethyl) benzamide (Compound A-1) (32%).

¹H NMR δ (ppm, CDCl₃): 8.72 (s, 2H); 8.74-8.57 (m, 4H); 6.72 (b, NH); 3.94 (q, 2H); 2.28 (m, 2H).

Mass Spectrum: [M+I]=374.

EXAMPLES OF BIOLOGICAL ACTIVITY OF THE COMPOUND OF GENERAL FORMULA (I)

Example A

In Vivo Test on *Alternaria brassicae* (Leaf Spot of Crucifers)

The active ingredient tested is prepared by potter homogenisation in a concentrated suspension type formulation at 100 g/l. This suspension is then diluted with water to obtain the desired active material concentration.

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per cm³). The spores are collected from a 12-13-day-old culture.

The contaminated radish plants are incubated for 6-7 days at about 18° C., under a humid atmosphere.

Grading is carried out 6 to 7 days after the contamination, in comparison with the control plants.

Under these conditions, good (at least 50%) is observed at a dose of 500 ppm with the compounds: A1.

The N-{1-methylcarbamoyl-2-[3-chloro-5-(trifluoromethyl)-2-pyridinyl]-ethyl}-4-phenylbenzamide disclosed by Patent Application WO 01/11965 (see compound 316 in Table D) showed poor effectiveness on *Alternaria brassicae*, and zero effectiveness on *Botrytis cinerea* at 330 ppm; the N-{1-ethylcarbamoyl-2-[3-chloro-5-(trifluoromethyl)-2-pyridinyl]ethyl}-3-nitrobenzamide also disclosed by Patent Application WO 01/11965 (see compound 307 in Table D) showed poor effectiveness on *Alternaria brassicae* and zero effectiveness on *Botrytis cinerea* at 330 ppm; the N-{1-ethylcarbamoyl-2-[3-chloro-5-(trifluoromethyl)-2-pyridinyl]-ethyl}-benzamide and the N-{1-methylcarbamoyl-2-[3-chloro-5-(trifluoromethyl)-2-pyridinyl]ethyl}-benzamide also disclosed by Patent Application WO 01/11965 (see compounds 304 and 314 in Table D) showed zero effectiveness on *Botrytis cinerea* at 330 ppm; and the N-{1-ethylcarbamoyl-2-[3-chloro-5-(trifluoromethyl)-2-pyridinyl]ethyl}-4-chlorobenzamide, the N-{1-ethylcarbamoyl-2-[3-chloro-5-(trifluoromethyl)-2-pyridinyl]ethyl}-2-bromobenzamide and the N-{1-methylcarbamoyl-2-[3-chloro-5-(trifluoromethyl)-2-pyridinyl]ethyl}-4-methoxybenzamide also disclosed by Patent Application WO 01/11965 (see compounds 306, 310 and 315 in Table D) showed zero effectiveness on *Botrytis cinerea* at 330 ppm.

The N-{[3-chloro-5-(trifluoromethyl)-2-pyridinyl]methyl}-5-thienylacetamide disclosed by Patent Application WO 01/11965 (see compound 101 in table B) showed poor efficacy against *Alternaria brassicae* and no efficacy against *Botrytis cinerea* and *Peronospora parasitica* at 330 ppm.

The invention claimed is:
1. A compound of general formula (I)

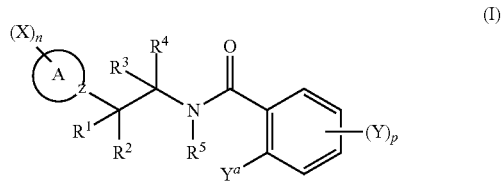

in which:
n is 1, 2, or 3;
p is 1, 2, 3 or 4;
A is a pyrimidine ring;
z is a carbon atom which can not be substituted by X;
each X is independently selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a $C_1$-$C_8$-halogenoalkyl having 1 to 5 halogen atoms, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl a phenyl, and a phenylamino;
$R^1$ and $R^2$ are independently selected from the group consisting of a hydrogen atom, a cyano group, a formyl group, a carboxy group, a carbamoyl group, a (hydroxyimino)-$C_1$-$C_6$-alkyl group, a $C_1$-$C_8$-alkyl, a $C_3$-$C_7$-cycloalkyl-$C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-halogenoalkyl having 1 to 5 halogen atoms, a $C_1$-$C_8$-alkylcarbamoyl, a di-$C_1$-$C_8$-alkylcarbamoyl, a $C_1$-$C_8$-alkoxycarbamoyl, a $C_1$-$C_8$-alkoxycarbonyl and a $C_1$-$C_8$-halogenoalkoxycarbonyl having 1 to 5 halogen atoms;

$R^3$ and $R^4$ are independently selected from the group consisting of a hydrogen atom, a cyano group, a formyl group, a carboxy group, a carbamoyl group, a (hydroxyimino)-$C_1$-$C_6$-alkyl group, a $C_1$-$C_8$-alkyl, $C_3$-$C_7$-cycloalkyl-$C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-halogenoalkyl having 1 to 5 halogen atoms, a $C_1$-$C_8$-alkylcarbamoyl, a di-$C_1$-$C_8$-alkylcarbamoyl, a $C_1$-$C_8$-alkoxycarbamoyl, a $C_1$-$C_8$-alkoxycarbonyl, and a $C_1$-$C_8$-halogenoalkoxycarbonyl having 1 to 5 halogen atoms;

$R^5$ is selected from the group consisting of a hydrogen atom, a $C_1$-$C_6$-alkyl, and a $C_3$-$C_7$-cycloalkyl;

each Y is independently selected from the group consisting of a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkoxy, a $C_1$-$C_8$-halogenoalkyl having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl and a (benzyloxyimino)-$C_1$-$C_6$-alkyl; and $Y^a$ is selected from the group consisting of a halogen atom, a cyano group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkoxy, a $C_1$-$C_8$-halogenoalkyl having 1 to 5 halogen atoms, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, and a (benzyloxyimino)-$C_1$-$C_6$-alkyl;

as well as its salts, N-oxides, and optically active isomers.

2. The compound of claim 1, wherein n is 1 or 2.

3. The compound of claim 1, wherein each X is independently selected from the group consisting of a hydrogen atom, a methyl group, a halogen atom, and a $C_1$-$C_8$-halogenoalkyl having 1 to 5 halogen atoms.

4. The compound of claim 1 wherein $R^1$ and $R^2$ are independently selected from the group consisting of a hydrogen atom, a $C_1$-$C_8$-alkyl, a $C_2$-$C_8$-alkenyl, a $C_2$-$C_8$-alkynyl, a $C_3$-$C_8$-cycloalkyl, a $C_3$-$C_7$-cycloalkyl-$C_1$-$C_8$-alkyl, a $C_3$-$C_8$-halogenocycloalkyl having 1 to 5 halogen atoms, and a $C_1$-$C_8$-halogenoalkyl having 1 to 5 halogen atoms.

5. The compound of claim 1, wherein $R^3$ and $R^4$ are independently selected from the group consisting of a hydrogen atom, a $C_1$-$C_8$-alkyl, a $C_2$-$C_8$-alkenyl, a $C_2$-$C_8$-alkynyl, a $C_3$-$C_8$-cycloalkyl, a $C_3$-$C_7$-cycloalkyl-$C_1$-$C_8$-alkyl, a $C_3$-$C_8$-halogenocycloalkyl having 1 to 5 halogen atoms, and a $C_1$-$C_8$-halogenoalkyl having 1 to 5 halogen atoms.

6. The compound of claim 1, wherein $Y^a$ is selected from the group consisting of a halogen atom, a pentafluoro-$\lambda^6$-sulfanyl group, a $C_1$-$C_8$-alkyl, a $C_1$-$C_8$-halogenoalkyl having 1 to 5 halogen atoms, and a $C_1$-$C_8$-halogenoalkoxy having 1 to 5 halogen atoms.

7. The compound of claim 1 wherein p is 1.

8. The compound of claim 1, wherein each Y is independently selected from the group consisting of a hydrogen atom and a halogen atom.

9. The compound of claim 1, wherein A is substituted in the 5-position.

10. A process for the preparation of the compound of claim 1, which comprises reacting a heterocyclylethylamine derivative of general formula (II) or one of its salts:

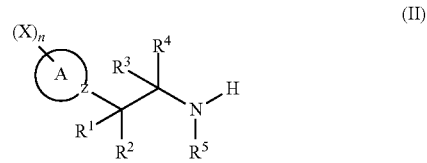

in which

A is a pyrimidine ring, each X is independently selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a $C_1$-$C_8$-halogenoalkyl having 1 to 5 halogen atoms, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_2$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl a phenyl, and a phenylamino;

n is 1, 2, or 3;

z is a carbon atom which can not be substituted by X;

$R^1$ and $R^2$ are independently selected from the group consisting of a hydrogen atom, a cyano group, a formyl group, a carboxy group, a carbamoyl group, a (hydroxyimino)-$C_1$-$C_6$-alkyl group, a $C_1$-$C_8$-alkyl, a $C_3$-$C_7$-cycloalkyl-$C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-halogenoalkyl having 1 to 5 halogen atoms, a $C_1$-$C_8$-alkylcarbamoyl, a di-$C_1$-$C_8$-alkylcarbamoyl, a $C_1$-$C_8$-alkoxycarbamoyl, a $C_1$-$C_8$-alkoxycarbonyl, and a $C_1$-$C_8$-halogenoalkoxycarbonyl having 1 to 5 halogen atoms;

$R^3$ and $R^4$ are independently selected from the group consisting of a hydrogen atom, a cyano group, a formyl group, a carboxy group, a carbamoyl group, a (hydroxyimino)-$C_1$-$C_6$-alkyl group, a $C_1$-$C_8$-alkyl, $C_3$-$C_7$-cycloalkyl-$C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-halogenoalkyl having 1 to 5 halogen atoms, a $C_1$-$C_8$-alkylcarbamoyl, a di-$C_1$-$C_8$-alkylcarbamoyl, a $C_1$-$C_8$-alkoxycarbamoyl, a $C_1$-$C_8$-alkoxycarbonyl, and a $C_1$-$C_8$-halogenoalkoxycarbonyl having 1 to 5 halogen, atoms; and $R^5$ is selected from the group consisting of a hydrogen atom, a $C_1$-$C_6$-alkyl, and a $C_3$-$C_7$-cycloalkyl;

with a carboxylic acid derivative of the general formula (III)

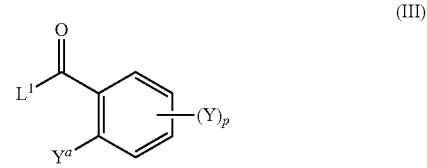

(III)

in which:

$Y^a$ is selected from the group consisting of a halogen atom, a cyano group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a $C_1$-$C_3$-alkenyl, a $C_1$-$C_8$-alkynyl, a $C_1$-$C_3$-alkoxy, a $C_1$-$C_8$-halogenoalkyl having 1 to 5 halogen atoms, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-halogenoalkenyloxy having 1 to 5 halogen atoms, a $C_1$-$C_8$-alkynyloxy, a $C_1$-$C_8$-halogenoalkynyloxy having 1 to 5 halogen atoms, a $C_1$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl:

Y is the same or different and is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkoxy, a $C_1$-$C_8$-halogenoalkyl having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, and a (benzyloxyimino)-$C_1$-$C_6$-alkyl; and p is 1, 2, 3 or 4;

$L^1$ is a leaving group selected from the group consisting of a halogen atom, a hydroxyl group, $-OR^{23}$, and $-OCOR^{23}$; wherein $R^{23}$ is selected from the group consisting of a $C_1$-$C_6$ alkyl, a $C_1$-$C_6$ haloalkyl, a benzyl, 4-methoxybenzyl, pentafluorophenyl, and a group of formula:

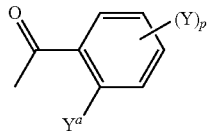

in the presence of a catalyst and, if $L^1$ is a hydroxyl group, in the presence of a condensing agent.

11. The process of claim 10, wherein $R^5$ is a hydrogen atom, and the process is completed by a further step according to the following reaction scheme:

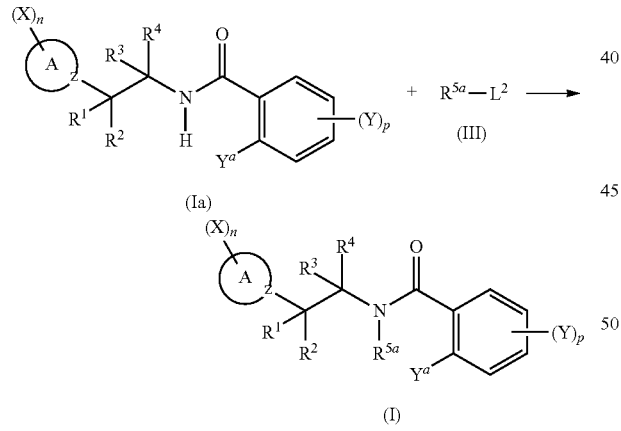

in which:
A is a pyrimidine ring;
each X is selected from the group consisting of a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a $C_1$-$C_8$-halogenoalkyl having 1 to 5 halogen atoms, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl a phenyl, and a phenylamino;

n is 1, 2, or 3;

z is a carbon atom which can not be substituted by X:

$R^1$ and $R^2$ are independently selected from the group consisting of a hydrogen atom, a cyano group, a formyl group, a carboxy group, a carbamoyl group, a (hydroxyimino)-$C_1$-$C_6$-alkyl group, a $C_1$-$C_8$-alkyl, a $C_3$-$C_8$-cycloalkyl-$C_1$-$C_8$-alkyl, a $C_2$-$C_8$-alkenyl, a $C_2$-$C_8$-alkynyl, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-halogenoalkyl having 1 to 5 halogen atoms, a $C_1$-$C_8$-alkylcarbamoyl, a di-$C_1$-$C_8$-alkylcarbamoyl, a $C_1$-$C_8$-alkoxycarbamoyl, a $C_1$-$C_8$-alkoxycarbonyl, and a $C_1$-$C_8$-halogenoalkoxycarbonyl having 1 to 5 halogen atoms;

$R^3$ and $R^4$ are independently selected from the group consisting of a hydrogen atom, a cyano group, a formyl group, a carboxy group, a carbamoyl group, a (hydroxyimino)-$C_1$-$C_6$-alkyl group, a $C_1$-$C_8$-alkyl, $C_3$-$C_7$-cycloalkyl-$C_1$-$C_3$-alkyl, a $C_2$-$C_8$-alkenyl, a $C_2$-$C_8$-alkynyl, a $C_1$-$C_8$-cycloalkyl, a $C_1$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-halogenoalkyl having 1 to 5 halogen atoms, a $C_1$-$C_8$-alkylcarbamoyl, a di-$C_1$-$C_8$-alkylcarbamoyl, a $C_1$-$C_8$-alkoxycarbamoyl, a $C_1$-$C_8$-alkoxycarbonyl, and a $C_1$-$C_8$-halogenoalkoxycarbonyl having 1 to 5 halogen atoms;

$Y^a$ is selected from the group consisting of a halogen atom, a cyano group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group a $C_1$-$C_8$-alkyl, a $C_2$-$C_8$-alkenyl, a $C_2$-$C_8$-alkynyl, a $C_1$-$C_8$-alkoxy, a $C_1$-$C_8$-halogenoalkyl having 1 to 5 halogen atoms, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_1$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl;

each Y is independently selected from the group consisting of a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkoxy, a $C_1$-$C_8$-halogenoalkyl having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_6$-alkoxyimino, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, and a (benzyloxyimino)-$C_1$-$C_6$-alkyl;

p is 1, 2, 3 or 4;

$R^{5a}$ is selected from the group consisting of a $C_1$-$C_6$-alkyl, and a $C_3$-$C_7$-cycloalkyl; and $L^2$ is a leaving group selected from the group consisting of a halogen atom, a 4-methyl phenylsulfonyloxy, and a methylsulfonyloxy;

comprising reacting a compound of formula (Ia) with a compound of formula (III) to provide a compound of formula (I).

12. A fungicide composition comprising an effective amount of the compound of claim 1 and an agriculturally acceptable support.

13. A method for combating the phytopathogenic fungi of crops comprising applying an effective and non-phytotoxic amount of the fungicide composition of claim 12 to the plant seeds or to the plant leaves and/or to the fruits of the plants or to the soil in which the plants are growing or in which it is desired to grow them.

* * * * *